# United States Patent [19]

Isbell et al.

[11] Patent Number: 5,849,935
[45] Date of Patent: Dec. 15, 1998

[54] METHOD FOR THE DEVELOPMENT OF δ-LACTONES AND HYDROXY ACIDS FROM UNSATURATED FATTY ACIDS AND THEIR GLYCERIDES

[75] Inventors: Terry A. Isbell, Elmwood, Ill.; Beth A. Plattner, Bloomington, Ind.; Robert Kleiman, Mesa, Ariz.

[73] Assignee: The United States of America as represented by the Secretary of Agriculture, Washington, D.C.

[21] Appl. No.: 534,810

[22] Filed: Sep. 27, 1995

[51] Int. Cl.$^6$ .................................................. C07D 309/00
[52] U.S. Cl. .......................... 549/273; 549/263; 554/148; 554/149; 568/700; 568/840; 568/876
[58] Field of Search ..................................... 554/148, 149; 549/263, 273; 568/200, 840, 876

[56] References Cited

U.S. PATENT DOCUMENTS

| 3,054,804 | 9/1962 | Swern et al. | 260/343.6 |
| 5,380,894 | 1/1995 | Burg et al. | 554/219 |

OTHER PUBLICATIONS

Showell, John S., et al. "Perchloric Acid Isomerizaition of Olicic Acid", J. Org. Chem., pp. 2697–2704, 1966.
Fore, Sara P., and Sumrell, Gene, "Some Derivatives of 5–Eicosenoic Acid", *The Journal of the American Oil Chemists Society*, pp. 581–584, 1970.
Morrison, Robert T., and Boyd, Robert N., *Organic Chemistry*, 3rd Edition, Chapt. 20, Allyn & Bacon, Boston, MA, pp. 672–674.
Isbell, Terry A. and Kleiman, Robert, "A Highly Regioselective Synthesis of Eicosanolactone and Docosanolactone from Meadowfoam Seed oil; Utilization of the Unique Chemical Structure of a new Crop's Fatty Acids", Abstract to be handed out at 21st World Congress and Exhibition of the International Socity for Fat Research (ISF), Oct. 1–5, 1995, The Hague, The Netherlands.

Ansell, M–F., and Palmer, M.H., "The Lactonisation of Olefinic Acids: the Use of Sulphuric and Trifluoroacetic Acids", *J. Chem. Soc.*, 1963, pp. 2640–2644.

Fujita, Tsutomu et al., "Syntheses of Dihydrolavandulol and its Related Compounds from Carboxylic Acis and Conjugated Dienes", *J. Chem. Tech. Biotechnol*, 1982, 32, pp. 476–484.

Sumell et al, J AOCS pp. 581–584, 1966.

Showell et al, J, Org Chem, pp. 2697–2704, 1970.

Showell et al., J Org Chem, pg. 2697–2704, 1966.

Fore et a., J AOCS, p. 581–584, 1970.

*Primary Examiner*—Gary Geist
*Assistant Examiner*—Deborah D. Carr
*Attorney, Agent, or Firm*—Randall E. Deck; M. Howard Silverstein; John D. Fado

[57] ABSTRACT

An improved process for the production of high yields of δ-lactones and 5-hydroxy fatty acids from unsaturated fatty acids which are free or esterified with glycerol is disclosed. The δ-lactones may be produced by reacting one or more $\Delta^5$ or $\Delta^6$ unsaturated fatty acids in the presence of an acid, clay or zeolite catalyst. Alternatively, the δ-lactones may be produced by reacting one or more triglycerides which are esters of glycerol with $\Delta^5$ or $\Delta^6$ unsaturated fatty acids with the same catalysts. Because the δ-lactones may be produced from the triglycerides of unsaturated fatty acids, the process may be practiced using naturally occurring plant oils directly, without the need for any preliminary steps of saponification. Optionally, the δ-lactones so formed may be further reacted with an alkali in an aqueous solution to produce 5-hydroxy fatty acids.

33 Claims, No Drawings

METHOD FOR THE DEVELOPMENT OF δ-LACTONES AND HYDROXY ACIDS FROM UNSATURATED FATTY ACIDS AND THEIR GLYCERIDES

BACKGROUND OF THE INVENTION

1. Field of the Invention

This invention relates to a novel process for producing δ-lactones and 5-hydroxy fatty acids from unsaturated fatty acids and their glycerides.

2. Description of the Prior Art

Gamma stearolactones and other small chain γ-lactones have been used as greases, antioxidants, perfumes, food flavors and dispersants for motor fuels. Techniques for the synthesis of both δ- and γ-lactones have been described throughout the chemical literature, and have included acid catalyzed reactions of unsaturated or olefinic acids.

Showell et al. (1968, J. Org. Chem., 33: 2697–2704) disclosed a process for the production of γ-stearolactone from oleic acid (18:1 $\Delta^9$) by perchloric acid catalysis. Delta-lactone intermediates were identified in the reaction mixture. Reactions using other fatty acids, namely undecylenic acid (11:1 $\Delta^{10}$) and erucic acid (22:1 $\Delta^{13}$) also produced γ-lactones under the same optimum conditions used for oleic acid (page 2702, paragraph 2).

High yields of δ-lactones have been achieved by the acid catalyzed reaction of substituted 4-hexenoic acid containing a carbocation stabilizing functionality as described by Fujita et al. (1982, J. Chem. Tech. Biotechnol., 32: 476–484). See Table 3.

Ansell and Palmer (1963, J. Chem. Soc., p. 2640–2644) described the production of γ- and δ-lactones from unsaturated five to eight carbon alkenoic acids in an acid or acidic solvent, using high molar equivalents of $H_2SO_4$ or trifluoroacetic acid ($CF_3CO_2H$) catalyst. In those trials where the proportion of δ-lactones was high (the ratio of δ to γ was high), yields were significantly reduced.

Unsaturated fatty acids have also been used in the past for the production of dimer acids by a variety of techniques, including clay catalyzed reactions, as reviewed by Johnson ["Dimerization and Polymerization," in: Fatty Acids, E. H. Pryde (ed.), AOCS, (1979), pages 343–352] and Leonard [in: Encyclopedia of Chemical Technology, Kirk-Othmer, John Wiley & Sons, third edition, volume 7, (1979)]. Depending upon the fatty acid feed, the dimer acids were produced together with monomer acids, and ranged in structure from acyclic to monocyclic to polycyclic.

Burg et al. (U.S. Pat. No. 5,380,894, issued Jan. 10, 1995) disclosed a process for the production of estolides from $\Delta^5$ and other unsaturated fatty acids in the presence of water and a clay catalyst. Burg et al. further disclosed hydrolyzing the estolides to form hydroxy fatty acids.

Hydroxy fatty acids have been described, and are useful as lubricants and greases, and in cosmetics, soaps, detergents, and fabric softeners. However, there is no domestic commercial source of hydroxy fatty acids currently available. The hydroxy fatty acids are commonly derived from castor oil which must be imported.

SUMMARY OF THE INVENTION

We have now invented an improved process for the production of high yields of δ-lactones and 5-hydroxy fatty acids from unsaturated fatty acids which are free or esterified with glycerol. The δ-lactones may be produced by reacting one or more $\Delta^5$ or $\Delta^6$ unsaturated fatty acids in the presence of an acid, clay or zeolite catalyst. Most unexpected however, we have discovered that the unsaturated fatty acids may be esterified with glycerol, and that the δ-lactones may be produced by reacting mono-, di- or triglycerides of $\Delta^5$ or $\Delta^6$ unsaturated fatty acids with the same catalysts. Because the δ-lactones may be produced from the triglycerides of unsaturated fatty acids, the instant process may be practiced using naturally occurring plant oils directly, without the need for any preliminary steps of saponification or steam splitting. Optionally, the δ-lactones so formed may be further reacted to produce 5-hydroxy fatty acids. These 5-hydroxy fatty acids may be produced by reaction of the δ-lactones with an alkali in an aqueous solution.

In accordance with this discovery, it is an object of this invention to provide a method of making δ-lactones in high yields.

It is another object of this invention to provide a method of making 5-hydroxy fatty acids in high yields.

Yet another object of this invention is to provide a method for making δ-lactones and/or 5-hydroxy fatty acids directly from triglycerides of unsaturated fatty acids.

Other objects and advantages of this invention will become readily apparent from the ensuing description.

DETAILED DESCRIPTION

Using the process of this invention, δ-lactones and 5-hydroxy fatty acids may be formed from $\Delta^5$ and $\Delta^6$ unsaturated fatty acids. Preferred starting materials include but are not limited to free and esterified unsaturated fatty acids of the formula (I):

$$R_1-CH=CH-(CH_2)_n-COOR_2 \qquad (I)$$

wherein n is 3 or 4, $R_1$ is hydrocarbon, particularly a $C_4$ to $C_{20}$ hydrocarbon, which may be saturated or unsaturated, and branched or straight chain, and $R_2$ is an H or a glyceride moiety which in combination with the fatty acid comprises a mono-, di- or triglyceride. Examples of particularly preferred unsaturated fatty acids which may be used herein include free and esterified 5-eicosenoic acid (20:1 $\Delta^5$), 5-docosenoic acid (22:1 $\Delta^5$), 5,13-docosadienoic acid (22:2, $\Delta^{5,13}$), petroselinic acid (16:1 $\Delta^6$), 18:1 $\Delta^5$ fatty acids, 18:2 $\Delta^{5,9}$ fatty acids, 18:3 $\Delta^{5,9,12}$ fatty acids, 20:3 $\Delta^{5,11,14}$ fatty acids, and 20:4 $\Delta^{5,11,14,17}$ fatty acids.

The $\Delta^5$ and $\Delta^6$ unsaturated fatty acids are naturally occurring in a variety of plant oils and may be conveniently obtained for use therefrom. Meadowfoam oil, having a high content of $\Delta^5$ unsaturated fatty acids (total fatty acids composed of approximately 60% 5-eicosenoic acid, 10% 5-docosenoic acid, 19% 5,13-docosadienoic acid, and less than 5% 18:1 $\Delta^5$ fatty acids), is particularly preferred as a source of the starting material. Without being limited thereto, other oils which may be used as sources, include pine oils (containing 18:1 $\Delta^5$, 18:2 $\Delta^{5,9}$, 18:3 $\Delta^{5,9,12}$, 20:3 $\Delta^{5,11,14}$, and 20:4 $\Delta^{5,11,14,17}$ fatty acids), marsh-marigold oils, or oils from the carrot family (i.e. coriander, dill and fennel).

As starting materials in the reaction of the invention, the unsaturated fatty acids may be provided in substantially pure form or, in the alternative, they may be provided as a mixture or in impure form. Moreover, although the starting unsaturated fatty acids may be free acids, we have surprisingly discovered that the reaction may also be conducted using fatty acids which are esterified with glycerol as mono-, di- or triglycerides while retaining the production of δ-lactones in high yields. Use of fatty acid triglycerides is particularly preferred. Because fatty acids generally occur as triglycerides in plant oils, the above-mentioned naturally occurring oils may be used directly in the reaction, thereby foregoing the need for any preliminary fatty acid isolation of the oil.

The practitioner skilled in the art will of course recognize that for products requiring a high degree of purity or uniformity, the oils may first be hydrolized to obtain free fatty acids for use as starting materials in the reaction. Hydrolysis of the oils to the fatty acids may be achieved using conventional splitting techniques or alkali splitting of fats. Suitable alkali splitting techniques include, for example, treatment with sodium methoxide, or sodium or potassium hydroxide [see "A.O.C.S. Tentative Method Ca 6b-53", in: Official and Tentative Methods of the American Oil Chemist's Society, third edition, AOCS, Chicago, Ill., (1973)]. Other conventional techniques including splitting with steam under pressure are also effective.

Once the starting material has been selected, the free or esterified unsaturated fatty acids are reacted in the presence of an acidic catalyst under conditions suitable to form δ-lactones. A variety of acidic catalysts may be used herein, including lewis acids, mineral acids, clays and zeolites, with concentrated mineral acids such as $HBrO_4$, $HIO_4$, and particularly $H_2SO_4$ and $HClO_4$ being preferred. Both $H_2SO_4$ and $HClO_4$ provide high yields of δ-lactones when reacting esterified unsaturated fatty acids in oils, although yields are reduced when using $H_2SO_4$ as a catalyst for free fatty acids. Use of $HClO_4$ is therefore preferred when reacting free fatty acids.

Conditions for δ-lactone formation are selected to minimize the formation of γ-lactones (favoring a high δ/γ ratio in the product) while maximizing δ-lactone yields. The catalyst should be present in a catalytically effective amount to produce δ-lactones from the unsaturated fatty acids. Without being limited thereto, in the preferred embodiment, the concentration of the catalyst should be between about 0.5 to 10 molar equivalents. For the purpose of this invention, a molar equivalent is defined herein as the moles of catalyst relative to the moles of starting fatty acids in the reaction mixture.

In accordance with a particularly preferred embodiment, the unsaturated fatty acids are provided in admixture with a solvent. Although its use is optional, the δ-lactone yield and/or the ratio of δ-lactones to γ-lactones in the product may be substantially increased if the reaction is conducted in the presence of a suitable solvent. Generally, maximum yields and δ/γ ratios are obtained using non-aqueous solvents having a relatively high dielectric constant, $\xi_r$, greater than approximately 1.8 debyes, and preferably about 8 to 9 debyes. Solvents having a greater dielectric constant may be employed provided that the solvent does not participate in the reaction. Suitable solvents for use herein include but are not limited to $CH_2Cl_2$, $CHCl_3$, hydrocarbons such as hexane and cyclohexane, and t-butanol, with $CH_2Cl_2$ being preferred. The volume of the solvent used may also significantly effect the ratio of δ- to γ-lactones in the product, with increased amounts of solvent relative to the unsaturated fatty acid generally providing greater δ/γ ratios. The actual volume of solvent will vary with the particular solvent selected, the starting fatty acids and reaction conditions, and may be determined by a practitioner skilled in the art. However, in the preferred embodiment using $CH_2Cl_2$, the volume of solvent should be greater than or equal to about 100%, most preferably at least about 500% (wherein the solvent is measured as wt %).

The temperature of the reaction will vary somewhat with the particular solvent selected, and the optimal temperature may be determined by a practitioner skilled in the art. Without being limited thereto, the preferred temperature of the reaction should be between about 20° to 50° C., and particularly between about 20° to 35° C. The reaction may optionally be conducted with solvent reflux. The reaction mixture is preferably agitated throughout the course of the reaction, such as by moderate stirring, rocking, or inert gas bubbling, to ensure adequate contact of all components. The time for the reaction will vary with the starting materials, choice of catalyst, solvent and temperature. Use of esterified unsaturated fatty acids or oils favors increased reaction rates. However, generally the reaction will be complete within 2 to 24 hours, usually within about 5 to 24 hours.

Using the process conditions described hereinabove, reaction yields of δ-lactones greater than 50% have been readily obtained, with yields from meadowfoam oil or its free fatty acids ranging from 70 to 90% after reaction for 24 hours. Moreover, a high regioselectivity for δ-lactone relative to γ-lactone has also been obtained, with δ/γ ratios ranging from about 10:1 up to 35:1 following the same reaction.

The resultant δ-lactones may be represented by the general formula (II):

$$\overset{\displaystyle \lceil \quad\quad O \quad\quad \rceil}{R-CH-(CH_2)_3-C=O} \quad\quad (II)$$

wherein R is a hydrocarbon which may be saturated or unsaturated, and branched or straight chain. Preferred δ-lactones include those formed by reaction of the above-mentioned $\Delta^5$ fatty acids from meadowfoam oil, such as eicosanolactone and docosanolactone formed from 5-eicosenoic and docosenoic acids, respectively.

Following the reaction, the δ-lactones may be separated and recovered by solvent extraction. For example, δ-lactones may be extracted by addition of hexane, with residual water removed from the hexane layer by mixing over a drying agent. Pure δ-lactones may be subsequently recovered from the hexane phase by crystallization at about 0° C., or in the alternative by vacuum (0.001 torr) wiped film distillation at about 150° C.

The δ-lactones so-produced may be used as an emollient in cosmetics and moisturizing creams. It is also envisioned that, as with the γ-lactones, the δ-lactones will be useful as biodegradable lubricants and greases, antioxidants, perfumes, food flavors and dispersants for motor fuels. In addition to these direct applications, the δ-lactones may also be used as intermediates for the production of other commercially valuable compounds, including but not limited to 5-hydroxy wax esters, 5-hydroxy amides including ethanolamide derivatives, and particularly 5-hydroxy fatty acids.

Production of 5-hydroxy fatty acids may be readily accomplished by reaction of the δ-lactones in the presence of an alkali in an aqueous solution. Moreover, although the δ-lactones may be isolated prior to this reaction, in the alternative the reaction may be performed directly upon the reaction mixture resulting from δ-lactone formation, thereby obviating any intermediate steps of separation and purification of the δ-lactones. Following completion of the reaction of unsaturated fatty acids to δ-lactones, hereinafter referred to as the initial reaction, an aqueous solution of an alkali may be added and the reaction mixture held under conditions effective to form hydroxy fatty acids. The particular alkali employed is not critical, and virtually any hydroxy moiety containing base will be operable. Preferred alkali for use herein include alkali metal hydroxides such as KOH and NaOH. The amount of alkali added should be approximately 1.5 moles in excess beyond the amount required to neutralize any acid catalyst remaining from the initial reaction.

To avoid interference in the production of hydroxy-fatty acids, any solvent from the initial reaction should be removed. While the solvent may be removed prior to addition of alkali, in the preferred embodiment it is removed concurrent with this reaction. Solvent removal may be effected, for example, by distillation during the course of the reaction. The vaporized solvent then may be collected in an overhead condenser operating without reflux. The temperature of the reaction should be between about 70° to 100° C. to maintain favorable reaction rates. The skilled practitioner will of course recognize that the temperature selected will vary with the solvent used in the initial reaction if it is to be removed by distillation.

The reaction may be terminated, generally in about 2 to 24 hours, by addition of an acid such as HCl or $CH_3COOH$ to quench or remove excess base. Sufficient acid should be added to lower the pH to between about 6 to 7, and no lower than about 5.5. The 5-hydroxy fatty acids may be subsequently recovered in pure form from the reaction mixture by extracting into ethyl acetate after the pH is adjusted to approximately 6. Extraction into this solvent may require heating the ethyl acetate to reflux on a steam bath or other heat source to dissolve any precipitate. Excess water is removed and the organic phase dried over sodium sulfate or other suitable drying agents, filtered and allowed to cool to room temperature then finally in an ice bath. Vacuum filtration provides the hydroxy fatty acids in greater than 70% yield. Alternatively, the ethyl acetate extraction step may be avoided by direct filtration of the pH adjusted solution. Recovery in this manner will provide a higher yield of a slightly less pure fraction of hydroxy fatty acids.

The resultant 5-hydroxy fatty acids may be represented by the general formula (III):

$$R\text{—COH—}(CH_2)_3\text{—COOH} \qquad (III)$$

wherein R is as described in formula (II). These hydroxy fatty acids may be used as biodegradable lubricants and greases, and in cosmetics, soaps, detergents, and fabric softeners.

As mentioned hereinabove, the δ-lactones may also be further reacted to produce hydroxy wax esters. In this embodiment, the δ-lactones are reacted with an alcohol in the presence of a catalytically effective amount of an acidic catalyst under conditions suitable to form hydroxy wax esters. A wide variety of organic alcohols may be reacted with the δ-lactones, including aromatic and normal or branched chain aliphatic alcohols. Hydroxy wax esters produced by reaction of a δ-lactone such as shown in formula (II) with an alcohol of the formula $R_2OH$, may be represented by the general formula (IV):

$$R\text{—COH—}(CH_2)_3\text{—COO—}R_2 \qquad (IV)$$

wherein $R_2$ is a hydrocarbon which may be saturated or unsaturated, branched or straight chain. As with the formation of 5-hydroxy fatty acids, this reaction may also be conducted using either δ-lactone which has been isolated or which remains in the initial reaction mixture.

Catalysts and conditions for production of hydroxy wax esters are similar to those described for the production of the δ-lactones. Suitable catalysts include, for example, mineral acids, lewis acids, clays and zeolites, with mineral acids such as $H_2SO_4$ and p-toluene sulfonic acid being preferred. The temperature for the reaction is not critical and may vary between about 20° to 150° C. Interestingly, when the reaction is conducted at higher temperatures, the amount of catalyst may be reduced or the catalyst may even be entirely omitted.

In the preferred embodiment, the 5-hydroxy wax esters are synthesized by mixing a slight excess of primary alcohol in the presence of about 0.01 equivalents of acid catalyst with δ-lactone (at the melting point of the lactone) and mixed thoroughly. An immediate precipitate will form and the whole reaction will solidify within about 15 minutes. At this point the reaction may be diluted in hexane and vacuum filtered to give near quantitative conversion of the δ-lactone to 5-hydroxy wax ester. Secondary, tertiary, hindered and other weaker nucleophilic alcohols will require longer reaction times and may not provide solid products.

Hydroxy wax esters produced in accordance with this invention may be used as moisturizers in cosmetics, biodegradable lubricants and dispersing agents for pigments and dyes in inks. Furthermore, the compounds possess strong surface active or chelating properties permitting their use as detergents and flocculants for heavy metals.

The δ-lactones may also be used to produce 5-hydroxy amides. The production of these compounds requires no catalyst to promote the reaction. Conversion takes place by mixing the δ-lactone with a slight excess of amine at the melting point of the δ-lactone. Primary amines provide an immediate precipitate upon addition of the amine signaling the completion of the reaction. Secondary, hindered and other weaker nucleophilic amines such as diethanol amine may require extended reaction times to reach completion. Upon consumption of the lactone, the reaction mixture may be diluted in hexane and vacuum filtered to remove any excess amine. This reaction may yield a near quantitative conversion to the 5-hydroxy amines.

The 5-hydroxy amides so produced may be useful as lubricants, cutting fluids, textile lubricants, hair care emollients, plasticizers and fabric softeners.

The following examples are intended only to further illustrate the invention and are not intended to limit the scope of the subject matter which is defined by the claims.

EXAMPLE 1

A series of reactions were conducted to examine the production of δ-lactones from $\Delta^5$ unsaturated fatty acids. Meadowfoam oil having a composition as described above was obtained from The Fanning Corp. (Chicago, Ill.) and the Oregon Meadowfoam Growers Association (Salem, Oreg.). Two to 10 g of meadowfoam oil were placed in a 2L reactor and equilibrated at the desired reaction temperature for 10 minutes. Reactions were run over a range of temperatures and using a variety of solvents as shown in Table 1. In some trials, no solvent was used. Concentrated $H_2SO_4$ or 70% $HClO_4$ were used as catalysts, and were added all at once to the reaction vessel in the molar equivalent amounts shown in Table 1, while stirring. Stirring was maintained throughout the course of the reaction. After 24 hours, the reaction was terminated by pouring into 50 ml of hexane and washed twice in 5 ml of 0.5M $Na_2HPO_4$. The residual water was removed from the hexane layer by mixing over a drying agent and then filtered and concentrated in vacuo. The δ-lactone yields and the ratio of δ/γ lactones were determined by HPLC and gas chromatography, respectively. The results are shown in Table 1.

EXAMPLE 2

To examine the effects of different solvent concentrations on yields and δ/γ ratios, the reaction of Example 1 was repeated using $CH_2Cl_2$ (2.171 molal) as solvent, 2 molar equivalents of $HClO_4$ as catalyst and a temperature of 35° C. with reflux for 3 hours. The results are shown in Table 2.

EXAMPLE 3

To illustrate the production of 5-hydroxy fatty acids, δ-lactones were produced in the same manner as described in Example 2 using 500% CH₂Cl₂, except that 102 g of meadowfoam oil was initially used (with the amounts of catalyst and solvent increased accordingly). The reaction mixture containing the δ-lactones was cooled to room temperature and a Dean-Stark trap placed on the flask. 43 g of KOH dissolved in 500 ml of water was added slowly to the flask and then the solvent removed as the reaction warmed to 80° C. Ethanol was added in 10 ml portions to minimize foaming. After 2–4 hours the reaction was quenched by cooling in an ice-bath and adding cold acetic acid solution (19.3 g in 500 ml H₂O) to the flask with vigorous stirring. Vacuum filtration and recrystallization from ethyl acetate gave 73% isolated mass yield of 5-hydroxy fatty acids as determined by mass balance.

It is understood that the foregoing detailed description is given merely by way of illustration and that modifications and variations may be made therein without departing from the spirit and scope of the invention.

TABLE 1

Delta Lactone Experiments

| Trials | Acid | Equivalent | Solvent | % Solvent | Temp. | δ/γ | % Lactone |
|---|---|---|---|---|---|---|---|
| 1 | H₂SO₄ | 0.5 | CH₂Cl₂ | 500% | Reflux | 8.9 | 10% |
| 2 | H₂SO₄ | 1.0 | CH₂Cl₂ | 500% | Reflux | 34.9 | 36% |
| 3 | H₂SO₄ | 2.0 | CH₂Cl₂ | 500% | Reflux | 11.3 | 63% |
| 4 | HClO₄ | 0.5 | CH₂Cl₂ | 500% | Reflux | 20.7 | 73% |
| 5 | HClO₄ | 1.0 | CH₂Cl₂ | 500% | Reflux | 17.7 | 82% |
| 6 | HClO₄ | 2.0 | CH₂Cl₂ | 500% | Reflux | 10.5 | 88% |
| 7 | HClO₄ | 1.0 | hexane | 500% | Reflux | 0.2 | 76% |
| 8 | HClO₄ | 1.0 | cyclo-hexane | 500% | Reflux | 0.1 | 96% |
| 9 | HClO₄ | 1.0 | CHCl₃ | 500% | Reflux | 0.2 | 92% |
| 10 | HClO₄ | 1.0 | ether | 500% | Reflux | 0.0 | 0 |
| 11 | HClO₄ | 1.0 | CH₃OH | 500% | Reflux | 0.0 | 0 |
| 12 | HClO₄ | 1.0 | hexane | 500% | 35° C. | 6.4 | 33% |
| 13 | HClO₄ | 1.0 | cyclo-hexane | 500% | 35° C. | 12.8 | 13% |
| 14 | HClO₄ | 1.0 | CHCl₃ | 500% | 35° C. | 21.7 | 52% |
| 15 | HClO₄ | 1.0 | CH₃OH | 500% | 35° C. | 0.0 | 0 |
| 16 | HClO₄ | 2.0 | | 0 | Room | 7.3 | 86% |
| 17 | HClO₄ | 3.18 | CH₂Cl₂ | 50% | Room | 10.4 | 88% |
| 18 | HClO₄ | 4.02 | CH₂Cl₂ | 100% | Room | 12.5 | 92% |
| 19 | HClO₄ | 6.96 | CH₂Cl₂ | 250% | Room | 16.4 | 91% |
| 20 | HClO₄ | 12.9 | CH₂Cl₂ | 500% | Room | 20.7 | 88% |
| 21 | HClO₄ | 1.35 | | 0 | Room | 10.0 | 68% |
| 22 | HClO₄ | 1.02 | | 0 | Room | 13.0 | 47% |
| 23 | HClO₄ | 0.57 | | 0 | Room | 19.2 | 23% |

TABLE 2

Delta Lactone Experiments

| Trials | Acid | Equivalent | Solvent | % Solvent | Temp. | δ/γ | % Lactone |
|---|---|---|---|---|---|---|---|
| 1 | HClO₄ | 2.04 | CH₂Cl₂ | 0 | Room | 7.7 | 78% |
| 2 | HClO₄ | 2.04 | CH₂Cl₂ | 50% | Room | 7.8 | 83% |
| 3 | HClO₄ | 2.13 | CH₂Cl₂ | 100% | Room | 16.2 | 80% |
| 4 | HClO₄ | 2.01 | CH₂Cl₂ | 250% | Room | 25.7 | 78% |
| 5 | HClO₄ | 2.01 | CH₂Cl₂ | 500% | Room | 38.5 | 75% |

We claim:

1. A method for making δ-lactones comprising reacting one or more mono-, di- or triglycerides comprising esters of glycerol with $\Delta^5$ or $\Delta^6$ unsaturated fatty acids in the presence of a catalytically effective amount of a catalyst selected from the group consisting of lewis acids, mineral acids, clays and zeolites, under conditions and for a period of time sufficient to form a δ-lactone of the formula:

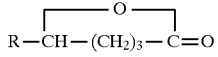

wherein R is a hydrocarbon which may be saturated or unsaturated, or branched or straight chain.

2. A method as described in claim 1 wherein said catalyst is a mineral acid selected from the group consisting of H₂SO₄, HClO₄, HBrO₄, and HIO₄.

3. A method as described in claim 2 wherein said mineral acid is HClO₄.

4. A method as described in claim 2 wherein said mineral acid is H₂SO₄.

5. A method as described in claim 1 wherein the amount of said catalyst is between about 0.5 and 10 molar equivalents.

6. A method as described in claim 1 wherein the temperature is between about 20° to 50° C.

7. A method as described in claim 6 wherein the temperature is between about 20° to 35° C.

8. A method as described in claim 1 wherein said mono-, di- or triglycerides are in a non-aqueous inert solvent having a dielectric constant greater than about 1.8.

9. A method as described in claim 8 wherein said solvent has a dielectric constant greater than about 8.

10. A method as described in claim 8 wherein said solvent is a hydrocarbon.

11. A method as described in claim 8 wherein said solvent is selected from the group consisting of methylene chloride, and chloroform.

12. A method as described in claim 1 further comprising reacting said δ-lactone with an alkali in an aqueous solution for a period of time effective to form a 5-hydroxy fatty acid of the formula:

13. A method as described in claim 12 wherein said mono-, di- or triglycerides are in a non-aqueous inert solvent having a dielectric constant greater than about 1.8, and said solvent is removed during the step of reacting said δ-lactone with said alkali.

14. A method as described in claim 13 wherein said solvent is removed by distillation.

15. A method as described in claim 12 wherein said alkali is an alkali metal hydroxide.

16. A method as described in claim 15 wherein said alkali is KOH.

17. A method as described in claim 12 further comprising adding a sufficient amount of acid to remove excess alkali and terminate the formation of said 5-hydroxy fatty acid.

18. A method as described in claim 1 further comprising reacting said δ-lactone with an alcohol of the formula $R_1$—OH in the presence of a catalytically effective amount of a catalyst selected from the group consisting of lewis acids, mineral acids, clays and zeolites, to form a hydroxy wax ester of the formula:

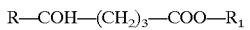

wherein $R_1$ is a hydrocarbon which may be saturated or unsaturated, or branched or straight chain.

19. A method as described in claim 1 wherein said unsaturated fatty acids are selected from the group consisting of 5-eicosenoic acid, 5-docosenoic acid, 5,13-docosadienoic acid, 18:1 $\Delta^5$ fatty acids, and petroselinic acid.

20. A method as described in claim 1 further comprising separating and recovering said δ-lactone.

21. A method for making 5-hydroxy fatty acids comprising:
   a. reacting in a single step one or more $\Delta^5$ or $\Delta^6$ unsaturated fatty acids in the presence of a catalytically effective amount of a catalyst selected from the group consisting of lewis acids, mineral acids, clays and zeolites, under conditions and for a period of time sufficient to form a δ-lactone of the formula:

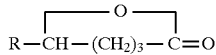

and b. reacting said δ-lactone with an alkali in an aqueous solution for a period of time effective to form a 5-hydroxy fatty acid of the formula:

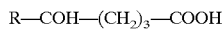

wherein R is a hydrocarbon which may be saturated or unsaturated, or branched or straight chain.

22. A method as described in claim 21 wherein said unsaturated fatty acids are in a non-aqueous inert solvent having a dielectric constant greater than about 1.8, and said solvent is removed during the step of reacting said δ-lactone with said alkali.

23. A method as described in claim 22 wherein said solvent has a dielectric constant greater than about 8.

24. A method as described in claim 22 wherein said solvent is a hydrocarbon.

25. A method as described in claim 22 wherein said solvent is selected from the group consisting of methylene chloride, and chloroform.

26. A method as described in claim 21 wherein said unsaturated fatty acids are selected from the group consisting of 5-eicosenoic acid, 5-docosenoic acid, 5,13-docosadienoic acid, 18:1 $\Delta^5$ fatty acids, and petroselinic acid.

27. A method as described in claim 21 wherein said catalyst is a mineral acid selected from the group consisting of $H_2SO_4$, $HClO_4$, $HBrO_4$, and $HIO_4$.

28. A method as described in claim 27 wherein said mineral acid is $HClO_4$.

29. A method as described in claim 27 wherein said mineral acid is $H_2SO_4$.

30. A method as described in claim 21 wherein the amount of said catalyst is between about 0.5 and 10 molar equivalents.

31. A method as described in claim 21 wherein the temperature is between about 20° to 50° C.

32. A method as described in claim 31 wherein the temperature is between about 20° to 35° C.

33. A method as described in claim 21 wherein the reaction of said $\Delta^5$ or $\Delta^6$ unsaturated fatty acids to form said δ-lactone does not introduce any functionalities into said R group.

* * * * *